United States Patent
Fujimoto et al.

(10) Patent No.: US 10,450,334 B2
(45) Date of Patent: *Oct. 22, 2019

(54) PHOTORESPONSIVE NUCLEOTIDE ANALOGUE HAVING PHOTOCROSSLINKING ABILITY

(71) Applicant: JAPAN ADVANCED INSTITUTE OF SCIENCE AND TECHNOLOGY, Nomi-shi, Ishikawa (JP)

(72) Inventors: Kenzo Fujimoto, Nomi (JP); Takashi Sakamoto, Nomi (JP); Yuya Tanaka, Nomi (JP)

(73) Assignee: JAPAN SCIENCE AND TECHNOLOGY AGENCY, Kawaguchi-Shi (JP)

( * ) Notice: Subject to any disclaimer, the term of this patent is extended or adjusted under 35 U.S.C. 154(b) by 408 days.

This patent is subject to a terminal disclaimer.

(21) Appl. No.: 14/780,187

(22) PCT Filed: Mar. 27, 2014

(86) PCT No.: PCT/JP2014/058988
§ 371 (c)(1),
(2) Date: Sep. 25, 2015

(87) PCT Pub. No.: WO2014/157565
PCT Pub. Date: Oct. 2, 2014

(65) Prior Publication Data
US 2016/0031918 A1    Feb. 4, 2016

(30) Foreign Application Priority Data
Mar. 28, 2013    (JP) .................................. 2013-070381

(51) Int. Cl.
| | |
|---|---|
| *C07H 21/02* | (2006.01) |
| *C07H 21/04* | (2006.01) |
| *C07D 209/88* | (2006.01) |
| *C07H 21/00* | (2006.01) |
| *C07D 209/86* | (2006.01) |
| *C07H 19/04* | (2006.01) |
| *C07F 9/572* | (2006.01) |
| *B01J 19/12* | (2006.01) |
| *C08F 232/08* | (2006.01) |

(52) U.S. Cl.
CPC ........... *C07F 9/5728* (2013.01); *B01J 19/121* (2013.01); *B01J 19/123* (2013.01); *C07D 209/86* (2013.01); *C07D 209/88* (2013.01); *C07H 19/04* (2013.01); *C07H 21/00* (2013.01); *C07H 21/02* (2013.01); *C07H 21/04* (2013.01); *C08F 232/08* (2013.01)

(58) Field of Classification Search
None
See application file for complete search history.

(56) References Cited

U.S. PATENT DOCUMENTS

| | | | |
|---|---|---|---|
| 2010/0274000 A1* | 10/2010 | Fujimoto | C07D 405/04 536/26.9 |
| 2016/0326207 A1* | 11/2016 | Fujimoto | C07H 21/04 |

FOREIGN PATENT DOCUMENTS

| | | |
|---|---|---|
| EP | 2 216 338 A1 | 8/2010 |
| JP | 5-507419 A | 10/1993 |
| JP | 3753938 B2 | 3/2006 |
| JP | 3753942 B2 | 3/2006 |
| JP | 4814904 B2 | 11/2011 |
| JP | 4940311 B2 | 5/2012 |
| WO | 92/02532 A1 | 2/1992 |
| WO | 2005/083073 A1 | 9/2005 |
| WO | 2009/066447 A1 | 5/2009 |
| WO | 2010/147673 A2 | 12/2010 |

OTHER PUBLICATIONS

Kashida et al., "Control of the Chirality and Helicity of Oligomers of Serinol Nucleic Acid (SNA) by Sequence Design" Angew. Chem. Int. Ed. 2011, vol. 50 pp. 1285-1288 (Year: 2011).*

(Continued)

*Primary Examiner* — Eric Olson
(74) *Attorney, Agent, or Firm* — Westerman, Hattori, Daniels & Adrian, LLP

(57) ABSTRACT

The present invention provides a new photoreactive compound which can be used in technologies for photoreactions of nucleic acid, and also provides a photoreactive crosslinking agent comprising the above photoreactive compound. A photoreactive compound represented by the following formula I can be used.

12 Claims, 2 Drawing Sheets

(56) References Cited

OTHER PUBLICATIONS

Notification of Transmittal of Translation of the International Preliminary Report on Patentability (FormPCT/IB/338) issued in counterpart International Application No. PCT/JP2014/058988. (17 pages).
Extended (supplementary) European Search Report dated Oct. 31, 2016, issued in counterpart European Patent Application No. 14773781.1. (6 pages).
International Search Report dated Jun. 10, 2014, issued in counterpart Application No. PCT/JP2014/058988 (2 pages).

* cited by examiner

PHOTORESPONSIVE NUCLEOTIDE ANALOGUE HAVING PHOTOCROSSLINKING ABILITY

TECHNICAL FIELD

The present invention relates to a photoreactive nucleobase-like structure capable of crosslinking with nucleic acid and the like, a photoreactive crosslinking agent having an alternative structure of deoxyribose and a photoreactive nucleotide-like compound (photoreactive nucleotide analogue) having photo crosslinking (light crosslinking) ability comprising the above nucleobase-like structure as a base moiety and the above alternative deoxyribose structure as a deoxyribose moiety.

BACKGROUND ART

Coupling and crosslinking a nucleic acid is a basic technique in the field of molecular biology. For example, coupling and crosslinking a nucleic acid is used in combination with hybridization in order to introduce a gene and detect a base sequence. Or, for example, in order to inhibit gene expression. Therefore, technologies for coupling and crosslinking a nucleic acid are extremely important not only for basic research in molecular biology but also for use in, for example, diagnosis and treatment in the field of medicine, or development and manufacture of therapeutic agents, diagnostic agents and the like, and development and manufacture of enzymes, microorganisms and the like in the field of industry and agriculture.

As the aforementioned technologies for coupling or crosslinking a nucleic acid, those in which photoreactions are used in the absence of enzymes have been gathering attention because the reactions have fewer restrictions in terms of time and spatial control, and may be performed under milder conditions than those used for common organic chemical reactions and the like.

Such technologies for photoreaction of nucleic acid include a photo coupling technology in which 5-cyanovinyldeoxyuridine is used (Patent Literature 1: Japanese Patent No. 3753938, Patent Literature 2: Japanese Patent No. 3753942), a photo crosslinking technology in which a modified nucleoside having a 3-vinylcarbazole structure at the base moiety is used (Patent Literature 3: Japanese Patent No. 4814904, Patent Literature 4: Japanese Patent No. 4940311).

LIST OF PRIOR ART DOCUMENTS

Patent Literatures

Patent Literature 1: Japanese Patent No. 3753938
Patent Literature 2: Japanese Patent No. 3753942
Patent Literature 3: Japanese Patent No. 4814904
Patent Literature 4: Japanese Patent No. 4940311

SUMMARY OF THE INVENTION

Problem to be Solved by the Invention

Due to the importance of technologies for photoreactions of nucleic acid, there is further need for a new compound which can be used in technologies for photoreactions of nucleic acid. An objective of the present invention is to provide a new photoreactive compound which can be used in technologies for photoreactions of nucleic acid and a photoreactive crosslinking agent comprising the above photoreactive compound.

Means for Solving the Problem

After extensively searching for a photoreactive compound serving as a photoreactive crosslinking agent which can be used in technologies for photoreactions of nucleic acid, the present inventors found that a compound having a vinylcarbazole backbone structure in place of the base moiety of a nucleobase and having a backbone structure represented by formula I below in place of the ribose and deoxyribose moiety can be a photoreactive crosslinking agent which can be used in such technologies for photoreactions of nucleic acid. Then the present invention was completed.

The compound according to the present invention comprises a backbone structure represented by formula I below, but not a sugar structure of ribose or deoxyribose which a natural nucleoside and nucleotide are supposed to have. Further, the compound according to the present invention does not comprise a base structure of a purine base or a pyrimidine base which natural nucleosides and nucleotides are supposed to have. That is, the compound according to the present invention has a chemical structure which does not show any structural similarity with those of natural nucleosides and nucleotides. Nevertheless, the compound according to the present invention can form a double helix with a single-stranded nucleic acid complimentary thereto when formed as a single-stranded nucleic acid, and forms photo crosslinking (light crosslinking) between one strand and the other strand in the double helix when a vinylcarbazole moiety forms a crosslink due to a photoreaction. Therefore, the photoreactive compound according to the present invention can be used as a photo crosslinking agent (light crosslinking agent) for a double helix capable of specifically reacting with a desired sequence.

Accordingly, the present invention includes the following (1) to.
(1) A photoreactive compound represented by the following formula I:

[Formula 1]

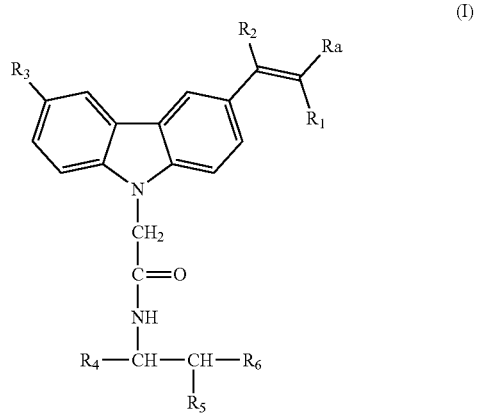

(wherein in formula I,
$R_a$ represents a cyano group, an amide group, a carboxyl group, a C2 to C7 alkoxycarbonyl group, a phosphono group, a sulfo group or a hydrogen atom, R1 and R2 each independently represent a cyano group, an amide group, a carboxyl group, a C2 to C7 alkoxycarbonyl group or a hydrogen atom, R3 is a hydrogen atom, a hydroxy group, a C1 to C3 alkoxy group, a C1 to C3 alkylsulfanyl group, a nitro group, a fluorine atom, a methyl fluoride group, a monovalent group of a C6 to C12 monocyclic or bicyclic aromatic compound, a monovalent group of a C6 to C12 monocyclic or bicyclic heterocyclic aromatic compound or a monovalent group represented by the following formula:

[Formula 2]

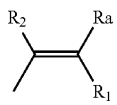

(wherein in the above formula, Ra, R1 and R2 represent groups selected from the groups listed for Ra, R1 and R2 described above with regard to Formula I independent of Ra, R1 and R2 described above with regard to the above formula I), R4 represents a hydrogen atom or a $Q_1$-O—$CH_2$-group, R5 represents an —O-$Q_1$ group, a hydrogen atom, a methyl group, or an ethyl group (provided that R5 represents an —O-$Q_1$ group when R4 is a hydrogen atom, and R5 represents a hydrogen atom, a methyl group or an ethyl group when R4 is a $Q_1$-O—$CH_2$-group), R6 represents an —O-$Q_2$ group, a —$CH_2$—O-$Q_2$ group or a —$CH(CH_3)$—O-$Q_2$ group, $Q_1$ represents a hydrogen atom, a phosphate group formed together with O attached to $Q_1$, a nucleotide or nucleic acid linked through a phosphodiester bond formed with a phosphate group formed together with O attached to $Q_1$ or a DMTr group, $Q_2$ represents a hydrogen atom, a phosphate group formed together with O attached to $Q_2$, a nucleotide or nucleic acid linked through a phosphodiester bond formed with a phosphate group formed together with O attached to $Q_2$ or a group represented by the following formula:

[Formula 3]

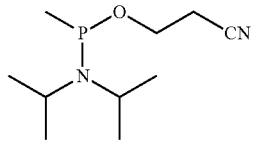

(wherein the above formula represents a monovalent group having a free valency at P),
or a group represented by the following formula:

[Formula 4]

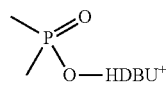

(wherein the above formula represents a monovalent group having a free valency at P)).

(2) The compound according to (1), represented by the following formula II:

[Formula 5]

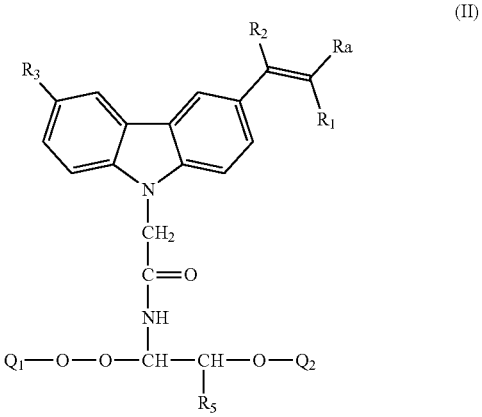

(II)

(wherein in formula II,

Ra represents a cyano group, an amide group, a carboxyl group, a C2 to C7 alkoxycarbonyl group, a phosphono group, a sulfo group or a hydrogen atom, R1 and R2 each independently represent a cyano group, an amide group, a carboxyl group, a C2 to C7 alkoxycarbonyl group or a hydrogen atom, R3 is a hydrogen atom, a hydroxy group, a C1 to C3 alkoxy group, a C1 to C3 alkylsulfanyl group, a nitro group, a fluorine atom, a methyl fluoride group, a monovalent group of a C6 to C12 monocyclic or bicyclic aromatic compound, a monovalent group of a C6 to C12 monocyclic or bicyclic heterocyclic aromatic compound or a monovalent group represented by the following formula:

[Formula 6]

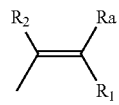

(wherein in the above formula, Ra, R1 and R2 represent groups selected from the groups listed for Ra, R1 and R2 described above with regard to formula I independent of Ra, R1 and R2 described above with regard to formula I), R5 represents a hydrogen atom, a methyl group or an ethyl group, $Q_1$ represents a hydrogen atom, a phosphate group formed together with O attached to $Q_1$, a nucleotide or nucleic acid linked through a phosphodiester bond formed with a phosphate group formed together with O attached to $Q_1$ or a DMTr group, $Q_2$ represents a hydrogen atom, a phosphate group formed together with O attached to $Q_2$, a nucleotide or nucleic acid linked through a phosphodiester bond formed with a phosphate group formed together with O attached to $Q_2$, a group represented by the following formula:

[Formula 7]

$$\begin{array}{c}\diagdown\\\diagup P\diagdown_{O}\diagdown\diagup^{CN}\\|\\N\\\diagup\diagdown\end{array}$$

(wherein the above formula represents a monovalent group having a free valency at P),
or a group represented by the following formula:

[Formula 8]

$$\begin{array}{c}\diagdown\\\diagup P\mathord{=}O\\|\\O\mathord{-}HDBU^+\end{array}$$

(wherein the above formula represents a monovalent group having a free valency at P)).

(3) The compound according to (1), represented by the following formula III:

[Formula 9]

(III)

[structure showing carbazole with R3, R2, Ra, R1 substituents, N-CH2-C(=O)-NH-CH(Q1-O)-CH(R7)-CH-O-Q2]

(wherein in formula III,
Ra represents a cyano group, an amide group, a carboxyl group, a C2 to C7 alkoxycarbonyl group, a phosphono group, a sulfo group or a hydrogen atom,
R1 and R2 each independently represent a cyano group, an amide group, a carboxyl group, a C2 to C7 alkoxycarbonyl group or a hydrogen atom,
R3 is a hydrogen atom, a hydroxy group, a C1 to C3 alkoxy group, a C1 to C3 alkylsulfanyl group, a nitro group, a fluorine atom, a methyl fluoride group, a monovalent group of a C6 to C12 monocyclic or bicyclic aromatic compound, a monovalent group of a C6 to C12 monocyclic or bicyclic heterocyclic aromatic compound or a monovalent group represented by the following formula:

[Formula 10]

$$\begin{array}{c}R_2\diagdown\quad\diagup Ra\\C\mathord{=}C\\\diagup\quad\diagdown R_1\end{array}$$

(wherein in the formula above, Ra, R1 and R2 represent groups selected from the groups listed for Ra, R1 and R2 described above with regard to formula I independent of Ra, R1 and R2 described above with regard to formula I),
R7 represents a hydrogen atom or a methyl group,
$Q_1$ represents a hydrogen atom, a phosphate group formed together with O attached to $Q_1$, a nucleotide or nucleic acid linked through a phosphodiester bond formed with a phosphate group formed together with O attached to $Q_1$ or a DMTr group,
$Q_2$ represents a hydrogen atom, a phosphate group formed together with O attached to $Q_2$, a nucleotide or nucleic acid linked through a phosphodiester bond formed with a phosphate group formed together with O attached to $Q_2$, a group represented by the following formula:

[Formula 11]

$$\begin{array}{c}\diagdown\\\diagup P\diagdown_{O}\diagdown\diagup^{CN}\\|\\N\\\diagup\diagdown\end{array}$$

(wherein the above formula represents a monovalent group having a free valency at P) or a group represented by the following formula:

[Formula 12]

$$\begin{array}{c}\diagdown\\\diagup P\mathord{=}O\\|\\O\mathord{-}HDBU^+\end{array}$$

(wherein the above formula represents a monovalent group having a free valency at P)).

(4) The compound according to (2) represented by the above formula II, wherein a backbone structure represented by the following formula IIa in formula II:

[Formula 13]

(IIa)

$$Q_1\mathord-O\mathord-O\mathord-\underset{\underset{R_5}{|}}{CH}\mathord-\underset{\underset{NH}{|}}{CH}\mathord-O\mathord-Q_2$$

is a D-threoninol structure represented by the following formula:

[Formula 14]

$$Q_1O\diagdown\underset{OQ_2}{\overset{NH}{\bigvee}}$$

an L-threoninol structure represented by the following formula:

[Formula 15]

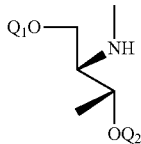

or a serinol structure represented by the following formula:

[Formula 16]

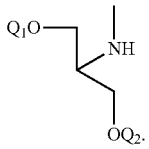

(5) The compound according to (3) represented by the above formula III, wherein a backbone structure represented by the following formula IIIa in Formula III:

[Formula 17]

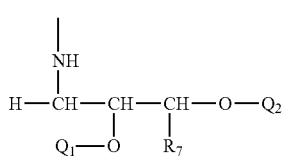
(IIIa)

is a (R)-3-amino-1,2-propanediol structure represented by the following formula:

[Formula 18]

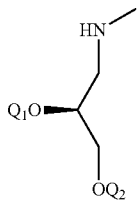

or an (S)-3-amino-1,2-propanediol structure represented by the following formula:

[Formula 19]

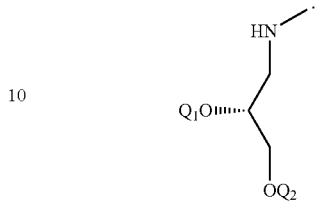

(6) The compound according to any one of (1) to (5), wherein R3 is a hydrogen atom, a hydroxy group, a C1 to C3 alkoxy group, a C1 to C3 alkylsulfanyl group, a nitro group, a fluorine atom, a trifluoromethyl group, a phenyl group, a 2-naphthyl group, a 2-indolyl group, a benzimidazole-2-yl group or a benzothiophene-2-yl group.

(7) The compound according to any one of (1) to (6), wherein $Q_1$ is a nucleotide or nucleic acid linked through a phosphodiester bond formed with a phosphate group formed together with O attached to $Q_1$, and $Q_2$ is a nucleotide or nucleic acid linked through a phosphodiester bond formed with a phosphate group formed together with O attached to $Q_2$.

(8) The compound according to any one of (1) to (6), wherein $Q_1$ is a hydrogen atom, and $Q_2$ is a hydrogen atom.

(9) The compound according to any one of (1) to (6), wherein $Q_1$ is a DMTr group, and $Q_2$ is a hydrogen atom, a phosphate group formed together with O attached to $Q_2$, a group represented by the following formula:

[Formula 20]

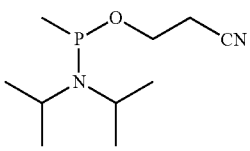

(wherein the above formula represents a monovalent group having a free valency at P),
or a group represented by the following formula:

[Formula 21]

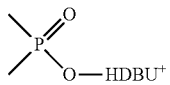

(wherein the above formula represents a monovalent group having a free valency at P).

(10) A photoreactive crosslinking agent comprising the compound according to any one of (1) to (9).

Further, the present invention also includes the following (11) to.

(11) A method of forming photo crosslinking with a nucleobase having a pyrimidine ring using the compound according to any one of (1) to (9).

(12) A method of forming photo crosslinking, the method comprising the steps of: hybridizing the compound according to (7) with a nucleic acid having a pyrimidine ring as a nucleobase to form a double helix, and performing photoirradiation on the double helix formed.

(13) A use of the compound according to any one of (1) to (9) for forming photo crosslinking with a nucleobase having a pyrimidine ring.

(14) A use of the compound according to (7) for forming photo crosslinking with other nucleic acids and the like having a pyrimidine ring as a nucleobase in a double helix formed by hybridization.

Further, the present invention also includes the following (21) to.

(21) A method of manufacturing a compound represented by the following formula VI, the method comprising performing a dehydration condensation reaction of a compound represented by the following formula IV with a compound represented by the following formula V:

[Formula 22]

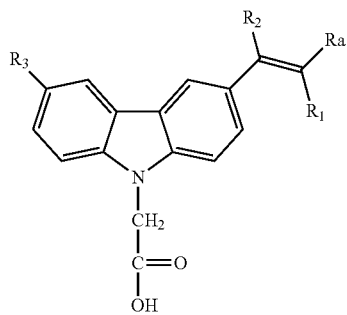

(IV)

(wherein in formula IV,

Ra represents a cyano group, an amide group, a carboxyl group, a C2 to C7 alkoxycarbonyl group, a phosphono group, a sulfo group or a hydrogen atom, R1 and R2 each independently represent a cyano group, an amide group, a carboxyl group, a C2 to C7 alkoxycarbonyl group or a hydrogen atom, R3 is a hydrogen atom, a hydroxy group, a C1 to C3 alkoxy group, a C1 to C3 alkylsulfanyl group, a nitro group, a fluorine atom, a methyl fluoride group, a monovalent group of a C6 to C12 monocyclic or bicyclic aromatic compound, a monovalent group of a C6 to C12 monocyclic or bicyclic heterocyclic aromatic compound or a monovalent group represented by the following formula:

[Formula 23]

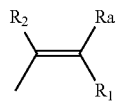

(wherein in the above formula, Ra, R1 and R2 represent a group selected from the groups listed for Ra, R1 and R2 described above with regard to formula IV independent of Ra, R1 and R2 described above with regard to formula IV));

[Formula 24]

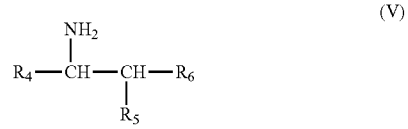

(V)

(wherein in formula V,

R4 represents a hydrogen atom or a $Q_1$-O—$CH_2$-group,

R5 represents an —O-$Q_1$ group, a hydrogen atom, a methyl group, or an ethyl group (provided that R5 represents an —O-$Q_1$ group when R4 is a hydrogen atom, and R5 represents a hydrogen atom, a methyl group or an ethyl group when R4 is a $Q_1$-O—$CH_2$-group), R6 represents an —O-$Q_2$ group, a —$CH_2$—O-$Q_2$ group or a —$CH(CH_3)$—O-$Q_2$ group, $Q_1$ represents a hydrogen atom, and $Q_2$ represents a hydrogen atom);

[Formula 25]

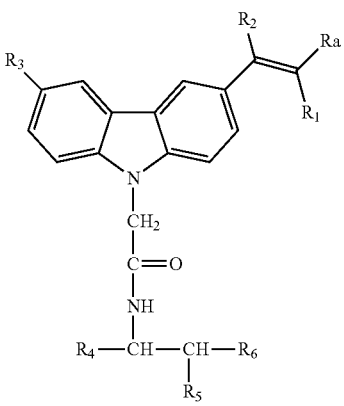

(VI)

(wherein in formula VI,

Ra, R1, R2, R3, R4, R5 and R6 represent the groups as described above with regard to the above formulas IV and V).

(22) A method of manufacturing a compound for synthesizing nucleic acid, the compound represented by the following formula VII, the method comprising using a compound represented by the following formula VI as an alternative molecule for a nucleoside molecule:

[Formula 26]

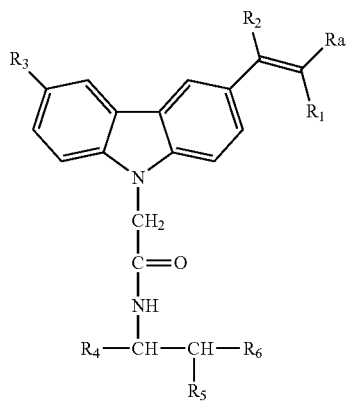

(VI)

(wherein in formula VI,

Ra represents a cyano group, an amide group, a carboxyl group, a C2 to C7 alkoxycarbonyl group, a phosphono group, a sulfo group or a hydrogen atom, R1 and R2 each independently represent a cyano group, an amide group, a carboxyl group, a C2 to C7 alkoxycarbonyl group or a hydrogen atom, R3 is a hydrogen atom, a hydroxy group, a C1 to C3 alkoxy group, a C1 to C3 alkylsulfanyl group, a nitro group, a fluorine atom, a methyl fluoride group, a monovalent group of a C6 to C12 monocyclic or bicyclic aromatic compound, a monovalent group of a C6 to C12 monocyclic or bicyclic heterocyclic aromatic compound or a monovalent group represented by the following formula:

[Formula 27]

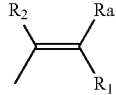

(wherein in the above formula, Ra, R1 and R2 represent groups selected from the groups listed for Ra, R1 and R2 described above with regard to formula VI independent of Ra, R1 and R2 described above with regard to formula VI), R4 represents a hydrogen atom or a $Q_1$-O—$CH_2$-group, R5 represents an —O-$Q_1$ group, a hydrogen atom, a methyl group or an ethyl group (provided that R5 represents an —O-$Q_1$ group when R4 is a hydrogen atom, and R5 represents a hydrogen atom, a methyl group or an ethyl group when R4 is a $Q_1$-O—$CH_2$-group), R6 represents an —O-$Q_2$ group, a —$CH_2$—O-$Q_2$ group or a —$CH(CH_3)$—O-$Q_2$ group, $Q_1$ represents a hydrogen atom, and $Q_2$ represents a hydrogen atom);

[Formula 28]

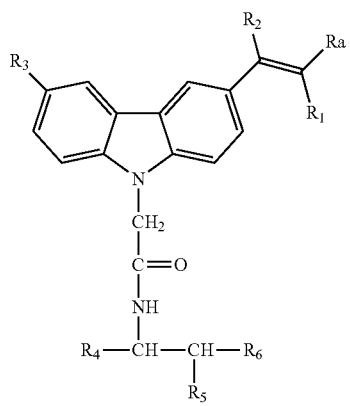

(VII)

(wherein in formula VII,

Ra, R1, R2, and R3 represent the groups described above in the above formula VI, R4 represents a hydrogen atom or a $Q_1$-O—$CH_2$-group, R5 represents an —O-$Q_1$ group, a hydrogen atom, a methyl group or an ethyl group (provided that R5 represents an —O-$Q_1$ group when R4 is a hydrogen atom, and R5 represents a hydrogen atom, a methyl group or an ethyl group when R4 is a $Q_1$-O—$CH_2$-group), R6 represents an —O-$Q_2$ group, a —$CH_2$—O-$Q_2$ group or a —$CH(CH_3)$—O-$Q_2$ group, $Q_1$ represents a DMTr group, $Q_2$ is a phosphate group formed together with O attached to $Q_2$, a group represented by the following formula:

[Formula 29]

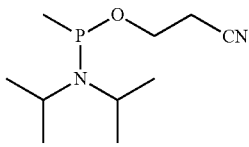

(wherein the above formula represents a monovalent group having a free valency at P)
or a group represented by the following formula:

[Formula 30]

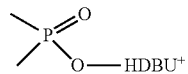

(wherein the above formula represents a monovalent group having a free valency at P).

(23) A method of manufacturing a photoreactive compound represented by the following formula I, the method comprising using a compound for synthesizing nucleic acid represented by the following formula VII as an alternative molecule for a nucleoside molecule:

[Formula 31]

(VII)

(wherein in formula VII,

Ra represents a cyano group, an amide group, a carboxyl group, a C2 to C7 alkoxycarbonyl group, a phosphono group, a sulfo group or a hydrogen atom, R1 and R2 each independently represent a cyano group, an amide group, a carboxyl group, a C2 to C7 alkoxycarbonyl group or a hydrogen atom, R3 is a hydrogen atom, a hydroxy group, a C1 to C3 alkoxy group, a C1 to C3 alkylsulfanyl group, a nitro group, a fluorine atom, a methyl fluoride group, a monovalent group of a C6 to C12 monocyclic or bicyclic aromatic compound, a monovalent group of a C6 to C12 monocyclic or bicyclic heterocyclic aromatic compound or a monovalent group represented by the following formula:

[Formula 32]

(wherein in the above formula, Ra, R1 and R2 represent groups selected from the groups listed for Ra, R1 and R2 described above with regard to formula VII independent of Ra, R1 and R2 described above with regard to formula VII), R4 represents a hydrogen atom or a $Q_1$-O—$CH_2$-group, R5 represents an —O-$Q_1$ group, a hydrogen atom, a methyl group or an ethyl group (provided that R5 represents an —O-$Q_1$ group when R4 is a hydrogen atom, and R5 represents a hydrogen atom, a methyl group or an ethyl group when R4 is a $Q_1$-O—$CH_2$-group), R6 represents an —O-$Q_2$ group, a —$CH_2$—O-$Q_2$ group or a —$CH(CH_3)$—O-$Q_2$ group, $Q_1$ represents a DMTr group, $Q_2$ is a phosphate group formed together with O attached to $Q_2$, a group represented by the following formula:

[Formula 33]

(wherein the above formula represents a monovalent group having a free valency at P)

or a group represented by the following formula:

[Formula 34]

(wherein the above formula represents a monovalent group having a free valency at P));

[Formula 35]

(I)

(wherein in formula I,

Ra, R1, R2, R3 represent the groups described above in the above formula VII,

R4 represents a hydrogen atom or a $Q_1$-O—$CH_2$-group,

R5 represents an —O-$Q_1$ group, a hydrogen atom, a methyl group or an ethyl group (provided that R5 represents an —O-$Q_1$ group when R4 is a hydrogen atom, and R5 represents a hydrogen atom, a methyl group or an ethyl group when R4 is a $Q_1$-O—$CH_2$-group), R6 represents an —O-$Q_2$ group, a —$CH_2$—O-$Q_2$ group or a —$CH(CH_3)$—O-$Q_2$ group, $Q_1$ represents a nucleotide or nucleic acid linked through a phosphodiester bond formed with a phosphate group formed together with O attached to $Q_1$, $Q_2$ represents a nucleotide or nucleic acid linked through a phosphodiester bond formed with a phosphate group formed together with O attached to $Q_2$).

Advantageous Effect of the Invention

The present invention provides a novel photoreactive crosslinking agent which can be used in technologies for photoreactions of nucleic acid. It is based on a novel chemical structure having neither a natural sugar structure nor base structure. According to the present invention, a photoreactive crosslinking agent showing a high conversion rate in a short time can be obtained by a simpler synthesis with a higher yield as compared with the conventional synthesis.

EMBODIMENTS OF THE INVENTION

Figure 1:
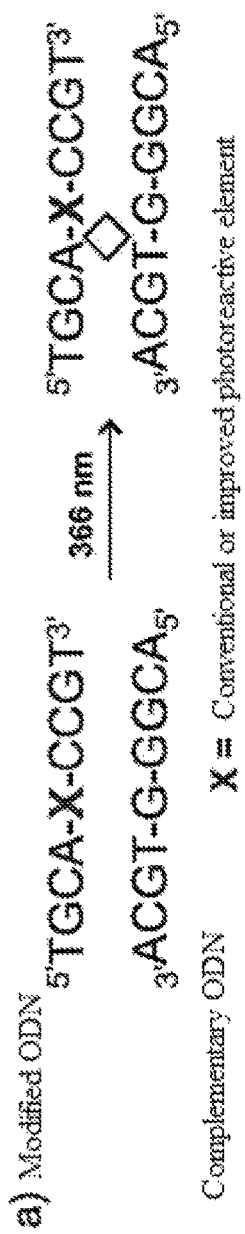
FIG. 1 shows procedures and results from experiments of forming a photo dimer by photo crosslinking.
Figure 1:
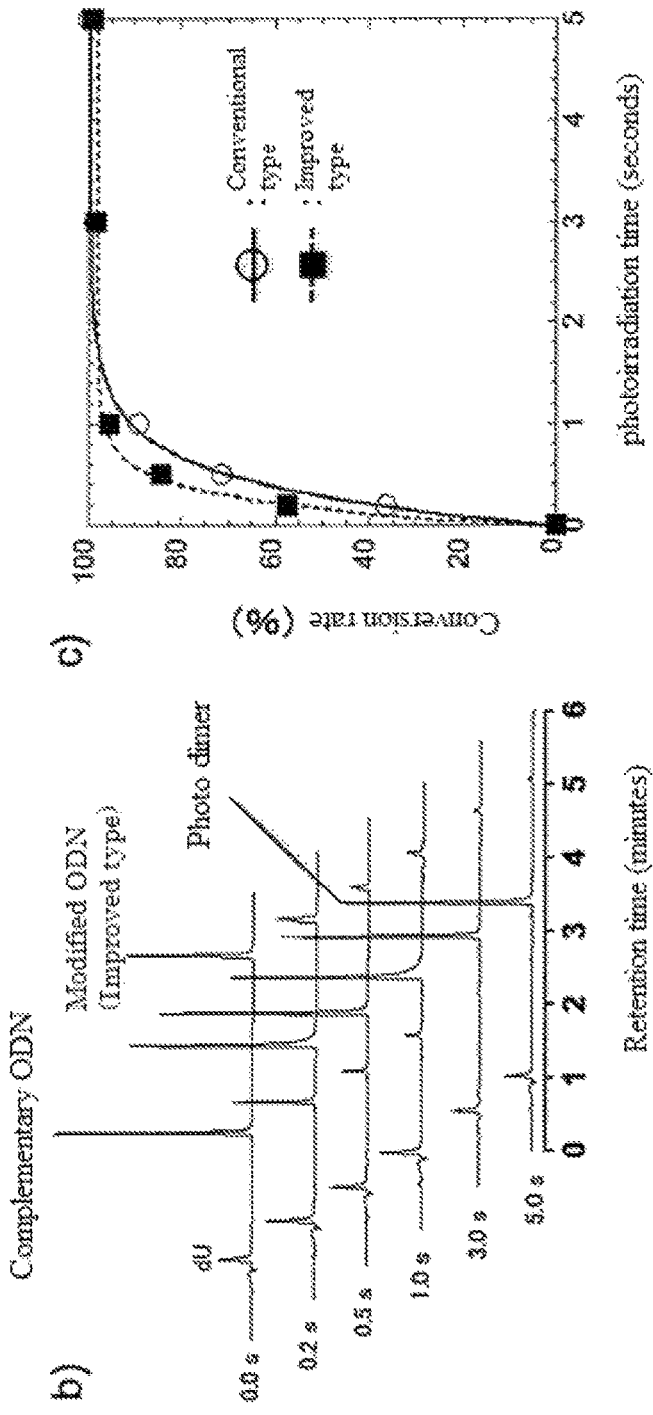

Below, the present invention will be described in detail with reference to specific embodiments. The present invention shall not be limited to the specific embodiments shown below.
[Structures of Compounds]
The present invention includes a photoreactive compound represented by the following formula I:

[Formula 36]

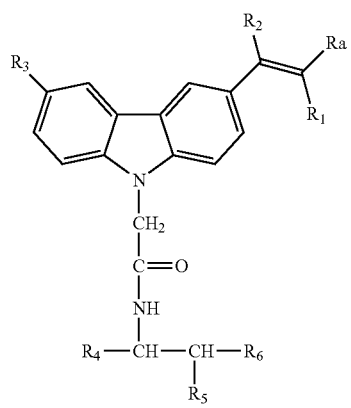

(I)

In the above formula I,
Ra is a cyano group, an amide group (—CO—$NH_2$), a carboxyl group, an alkoxycarbonyl group, a phosphono group (—PO(OH)$_2$), a sulfo group (—$SO_2$—(OH)) or a hydrogen atom, and preferably a cyano group, an amide group, a carboxyl group, an alkoxycarbonyl group or a hydrogen atom, and more preferably a cyano group, an amide group, a carboxyl group or an alkoxycarbonyl group. An alkoxycarbonyl group preferably of C2 to C7, more preferably of C2 to C6, more preferably of C2 to C5, more preferably of C2 to C4, more preferably of C2 to C3, in particular preferably of C2 can be used.

In the above formula I,
R1 and R2 are each independently a cyano group, an amide group, a carboxyl group, an alkoxycarbonyl group or a hydrogen atom, preferably a cyano group, an amide group, a carboxyl group, an alkoxycarbonyl group or a hydrogen atom, and more preferably a cyano group, an amide group, a carboxyl group or an alkoxycarbonyl group. An alkoxycarbonyl group preferably of C2 to C7, more preferably of C2 to C6, more preferably of C2 to C5, more preferably of C2 to C4, more preferably of C2 to C3, in particular preferably of C2 can be used.

In the above formula I,
R3 is a hydrogen atom, a hydroxy group, a C1 to C3 alkoxy group, a C1 to C3 alkylsulfanyl group, a nitro group, a fluorine atom, a methyl fluoride group, a monovalent group of a C6 to C12 monocyclic or bicyclic aromatic compound, a monovalent group of a C6 to C12 monocyclic or bicyclic heterocyclic aromatic compound or a monovalent group represented by the following formula:

[Formula 37]

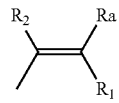

(wherein in the formula above, Ra, R1 and R2 represent groups selected from the groups listed for Ra, R1 and R2 described above with regard to formula I independent of Ra, R1 and R2 described above with regard to formula I).

In a preferred embodiment, R3 may be a hydrogen atom, a hydroxy group, a C1 to C3 alkoxy group, a C1 to C3 alkylsulfanyl group, a nitro group, a fluorine atom, a trifluoromethyl group, a phenyl group, a 2-naphthyl group, a 2-indolyl group, a benzimidazole-2-yl group or a benzothiophene-2-yl group.

In a preferred embodiment, for example, the groups listed below can be used as R3 (wherein wavy lines indicate the positions of free valency).

[Formula 38]

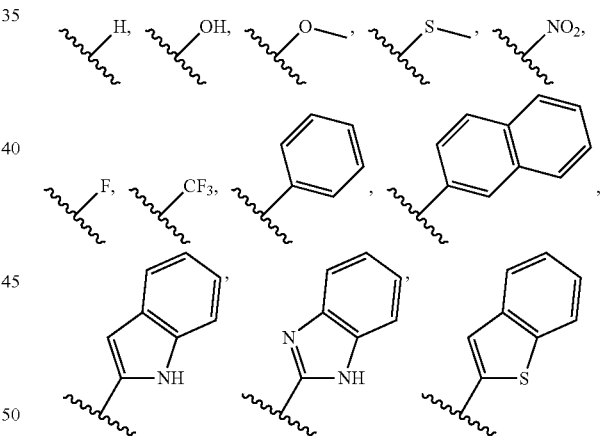

In the above formula I,
R4 represents a hydrogen atom or a $Q_1$-O—$CH_2$-group,
R5 represents an —O-$Q_1$ group, a hydrogen atom, a methyl group or an ethyl group
(provided that R5 represents an —O-$Q_1$ group when R4 is a hydrogen atom, and
R5 represents a hydrogen atom, a methyl group or an ethyl group when R4 is a $Q_1$-O—$CH_2$-group),
R6 represents an —O-$Q_2$ group, a —$CH_2$—O-$Q_2$ group or a —CH($CH_3$)—O-$Q_2$ group.

The above $Q_1$ represents a hydrogen atom, a phosphate group formed together with O attached to $Q_1$, a nucleotide or nucleic acid linked through a phosphodiester bond formed with a phosphate group formed together with O attached to $Q_1$ or a DMTr group, $Q_2$ represents a hydrogen atom, a phosphate group formed together with O attached to $Q_2$, a nucleotide or nucleic acid linked through a phosphodiester bond formed with a phosphate group formed together with O attached to $Q_2$, a group represented by the following formula:

[Formula 39]

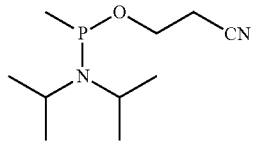

(wherein the above formula represents a monovalent group having a free valency at P)

or a group represented by the following formula:

[Formula 40]

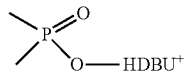

(wherein the above formula represents a monovalent group having a free valency at P).

In a preferred embodiment, in the above formula I, R4 may be a $Q_1$-O—$CH_2$-group, and R5 may be a hydrogen atom, a methyl group or an ethyl group, and R6 may be an —O-$Q_2$ group. In this case, the compound represented by the above formula I is represented by the following formula II:

[Formula 41]

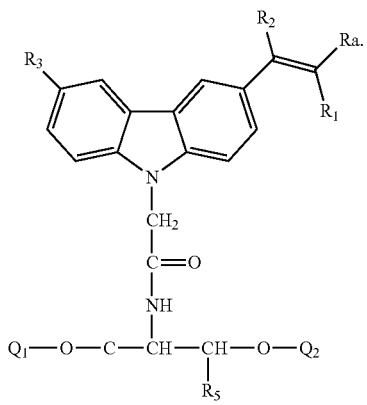

(II)

The backbone structure represented by the following formula IIa:

[Formula 42]

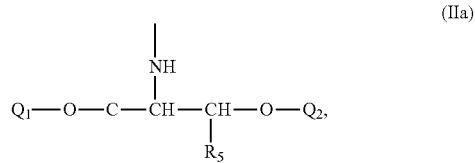

(IIa)

which is a partial structure in the above formula II, may preferably be a D-threoninol structure represented by the following formula:

[Formula 43]

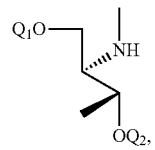

an L-threoninol structure represented by the following formula:

[Formula 44]

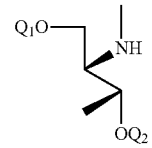

or a serinol structure represented by the following formula:

[Formula 44]

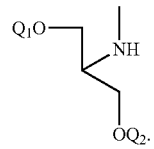

In a preferred embodiment, in the above formula I, R4 may be a hydrogen atom, and R5 may be an —O-$Q_1$ group, and R6 may be a —$CH_2$—O-$Q_2$ group or a —CH($CH_3$)—O-$Q_2$ group (that is, R6 may be a —CH(R7)-O-$Q_2$ group provided that R7 is a hydrogen atom or a methyl group). In this case, the compound represented by the above formula I is represented by the following formula III:

[Formula 46]

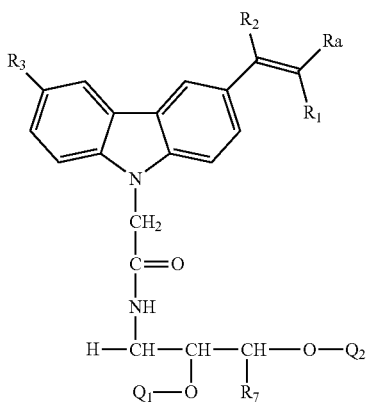

(III)

The backbone structure represented by the following formula IIIa:

[Formula 47]

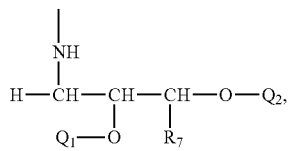

(IIIa)

which is a partial structure in the above formula III, may preferably be an (R)-3-amino-1,2-propanediol structure represented by the following formula:

[Formula 48]

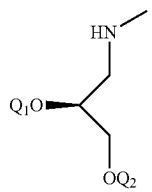

or an (S)-3-amino-1,2-propanediol structure represented by the following formula:

[Formula 49]

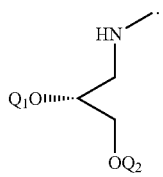

[Modified Nucleic Acid and the Like]

In a preferred embodiment, $Q_1$ may be a nucleotide or nucleic acid linked through a phosphodiester bond formed with a phosphate group formed together with O attached to $Q_1$ and $Q_2$ may be a nucleotide or nucleic acid linked through a phosphodiester bond formed with a phosphate group formed together with O attached to $Q_2$. That is, the compound represented by the above formula I may be a nucleic acid or oligonucleotide in which a photoresponsive artificial nucleotide analogue with a characteristic structure is incorporated into a sequence (which may also be referred to as a modified nucleic acid or a modified oligonucleotide according to the present invention, or a modified nucleic acid and the like according to the present invention). Further, in the modified nucleic acid and the like according to the present invention, a photoresponsive artificial nucleotide analogue having a characteristic structure may be located at an end of a sequence. In this case, the resulting nucleotide or nucleic acid is linked through a phosphodiester bond formed with a phosphate group formed together with O attached to $Q_1$ or $Q_2$ only at a side of either $Q_1$ or $Q_2$.

[Nucleoside Analogue]

In a preferred embodiment, $Q_1$ and $Q_2$ may be hydrogen atoms. That is, the compound represented by the above formula I may be a photoresponsive artificial nucleoside analogue molecule having a characteristic structure (which may be referred to as the nucleoside analogue according to the present invention).

[Nucleotide Analogue]

In a preferred embodiment, $Q_1$ may be a phosphate group formed together with O attached to $Q_1$, and $Q_2$ may be a hydrogen atom. That is, the compound according to the above formula I may be a photoresponsive artificial nucleotide analogue molecule having a characteristic structure (which may be referred to as the nucleotide analogue according to the present invention).

[Monomer for Synthesizing Modified Nucleic Acid]

In a preferred embodiment, $Q_1$ may be a DMTr group, and $Q_2$ may be a phosphate group formed together with O attached to $Q_2$, a nucleotide or nucleic acid linked through a phosphodiester bond formed with a phosphate group formed together with O attached to $Q_2$, a group represented by the following formula:

[Formula 50]

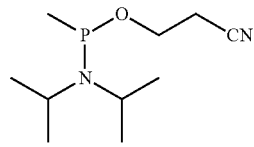

(wherein the above formula represents a monovalent group having a free valency at P), or a group represented by the following formula:

[Formula 51]

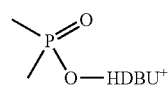

(wherein the above formula represents a monovalent group having a free valency at P).

That is, the compound represented by the above formula I may be a monomer having a characteristic structure for synthesizing a photoresponsive modified nucleic acid (which may be referred to as the monomer for synthesizing modified nucleic acid according to the present invention). A monomer having such a structure will serve as a reagent for synthesizing nucleic acid which can be used with the phosphoroamidite method and the H-phosphonate method, as is well known.

Examples the monomer for synthesizing modified nucleic acid as described above can include the following monomers.

[Formula 52]

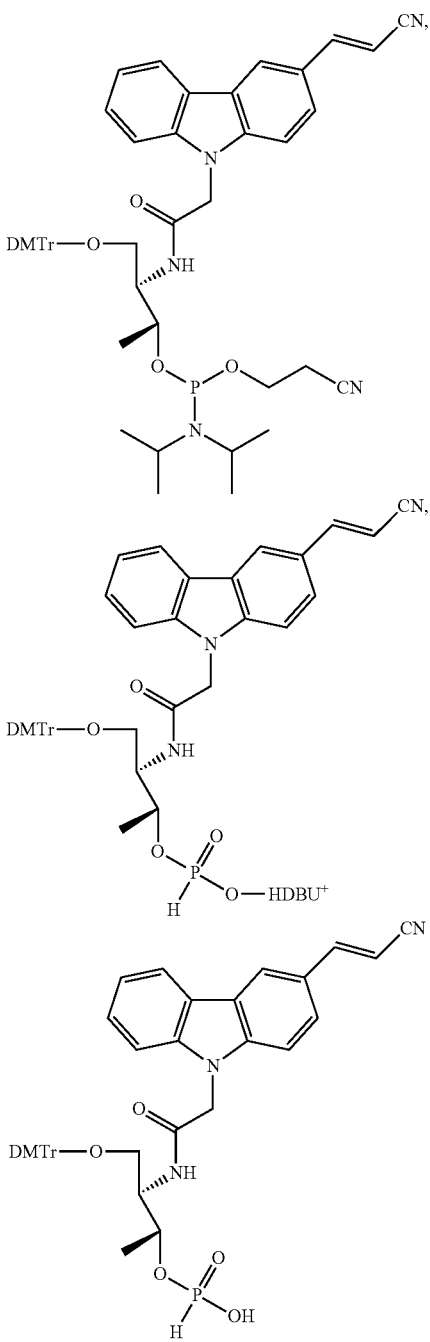

[Formation of Photo Crosslinking]

The modified nucleic acid and the like according to the present invention can hybridize with a single-stranded nucleic acid complementary thereto to form a double helix when used as a single-stranded nucleic acid. There is no particular limitation for the nucleobase in a position where base pairing should be formed with a vinylcarbazole structural moiety in a complementary strand when forming a double helix. Any nucleobase can be selected therefor. When the double helix formed is photoirradiated, a crosslink can be formed by a photoreaction between nucleic acid strands which form the double helix. This photo crosslinking is formed between a vinylcarbazole structure and a nucleobase located at a position in a complementary strand where base pairing is to be formed with a nucleobase located at one base toward the 5' end in a sequence from a position where the vinylcarbazole structure moiety is located as a nucleobase in the sequence. In other words, this photo crosslinking is formed between a vinylcarbazole structure and a nucleobase located at one base toward the 3' end in a sequence from a nucleobase located at a position in the complementary strand where base pairing is otherwise to be formed with the vinylcarbazole structure moiety.

A corresponding base with which a vinylcarbazole structure of the photoreactive compound according to the present invention can form photo crosslinking has a pyrimidine ring. Meanwhile, the photoreactive artificial nucleobase according to the present invention does not form photo crosslinking with a base having a purine ring. That is, in the case of natural nucleobases, the photo-crosslinking compound according to the present invention forms photo crosslinking with cytosine, uracil and thymine, but does not form photo crosslinking with guanine and adenine, showing strong specificity.

When used as a photoreactive modified nucleic acid and the like (a photo-crosslinking modified nucleic acid and the like), the photoreactive compound according to the present invention can hybridize with a sequence having a base sequence complementary to the modified nucleic acid and the like to form a double helix. Therefore, a photo crosslinking reaction (light crosslinking reaction) can be allowed only on a specific target sequence. That is, very high sequence specificity can be achieved by designing a sequence with the photo crosslinking agent compound according to the present invention if desired.

Irradiating light for photo crosslinking is preferably a light having a wavelength of, in general, between 350 and 380 nm, preferably between 360 and 370 nm, more preferably of 366 nm. In particular, it is preferably a laser beam with a single wavelength of 366 nm.

Photo cleavage can further be performed by photo irradiation after photo crosslinking. That is, the photoreactive compound according to the present invention can allow for reversible photo crosslinking, and can be used as a reversible photo crosslinking agent.

For the irradiating light for photo cleavage, a light including a light component having a wavelength of, in general, between 330 and 370 nm, preferably between 330 and 360 nm can be used. Further, in a preferred embodiment, a light including a light component having a wavelength of 366 nm, and in particular, a laser beam with a single wavelength of 366 nm can be used.

In a preferred embodiment, photoreactions for the above photo crosslinking and photo cleavage can be performed by irradiation of a light including a light component having a wavelength of between 350 and 370 nm, and preferably it can be performed using a laser beam with a single wavelength of 366 nm. Photoreactions for both photo crosslinking and photo cleavage can be performed with the same light source as long as a light having a wavelength in the above range is used. Therefore, it is advantageous in that two light sources need not to be provided. In a case of using a light having a wavelength in the above range, photoreactions for photo crosslinking and photo cleavage can be promoted in either direction by controlling temperature conditions. In order to promote a photo crosslinking reaction, photoirradiation is performed at a temperature of, in general, between 0 and 50° C., preferably between 0 and 40° C., more preferably between 0 and 30° C., more preferably between 0 to 20° C., more preferably between 0 and 10° C., more preferably between 0 and 5° C., and in particular preferably at 0° C. In order to promote a photo cleavage reaction, photoirradiation is performed at a temperature of, in general, between 60 and 100° C., preferably between 60 and 90° C., more preferably between 70 and 90° C.

There is no particular limitation on pH, temperature, salt concentrations and the like because the photo crosslinking and photo cleavage according to the present invention use a photoreaction. Therefore, photoirradiation can be performed in a solution at a pH, temperature and salt concentration where a biopolymer such as nucleic acid and the like can stably exist.

The photo crosslinking and photo cleavage according to the present invention progresses very rapidly. For example, the photoreaction would progress as rapidly as 1 second (photoirradiation at 366 nm) under conditions where it would take several hours in a case of psoralen which is known as a photoreactive compound (photoirradiation at 350 nm). That is, in a case where the photo crosslinking agent according to the present invention is used, a photoreaction can be promoted to form photo crosslinking by photoirradiation for several seconds, for example, 1 to 9 seconds, 1 to 7 seconds, 1 to 5 seconds or 1 to 3 seconds.

[Comparison with the Conventional Photoresponsive Artificial Nucleotide Having a Sugar Structure]

The present inventors have been studying artificial nucleotide structures having a structure of ribose or deoxyribose as photoresponsive artificial nucleotides for many years (refer to Patent Literatures 1 to 4). Nonetheless, as described above, the compound according to the present invention can be used as in the case of a photoresponsive artificial nucleotide to promote a photo crosslinking reaction even though it does not comprise structures of ribose and deoxyribose. That is, the outstanding properties disclosed in Patent Literature 4 (Japanese Patent No. 4940311) by the present inventors can similarly be achieved despite not having structures of ribose and deoxyribose. Indeed, the compound according to the present invention shows an advantageous effect of a higher conversion rate (that is, a rate of photo crosslinking formation) in a shorter duration of photoirradiation as compared with the conventional photoresponsive artificial nucleotide (photo crosslinking agent) having a structure of deoxyribose, even in a case where the same vinylcarbazole structure is included.

[Synthesis of Photoresponsive Artificial Nucleoside Analogue Molecules]

The photoresponsive artificial nucleoside analogue molecule according to the present invention can be synthesized in accordance with the synthetic pathway shown in Scheme 1 described below.

According to the synthetic pathway in Scheme 1, the carboxylic acid represented by the following formula IV is synthesized from the modified vinylcarbazole molecule represented by the following formula VIII:

[Formula 53]

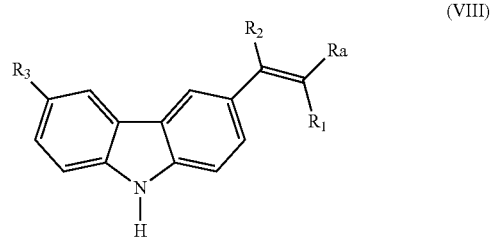
(VIII)

[Formula 54]

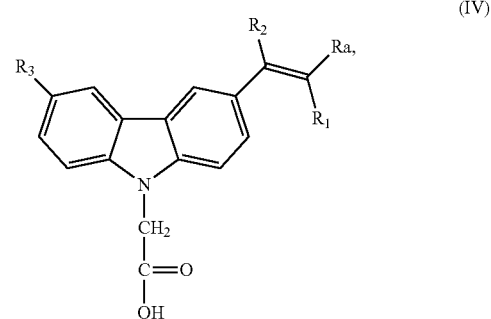
(IV)

which is then subjected to a dehydration condensation reaction with the amine represented by the following formula V to obtain the photoresponsive artificial nucleoside analogue molecule represented by the following formula VI:

[Formula 55]

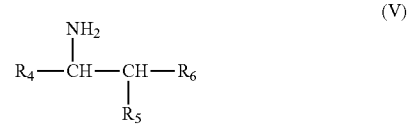
(V)

(wherein in formula V,

R4 represents a hydrogen atom or a $Q_1$-O—$CH_2$-group,

R5 represents an —O-$Q_1$ group, a hydrogen atom, a methyl group or an ethyl group (provided that R5 represents an —O-$Q_1$ group when R4 is a hydrogen atom, and R5 represents a hydrogen atom, a methyl group or an ethyl group when R4 is a $Q_1$-O—$CH_2$-group), R6 represents an —O-$Q_2$ group, a —$CH_2$—O-$Q_2$ group or a —$CH(CH_3)$—O-$Q_2$ group, $Q_1$ represents a hydrogen atom, and $Q_2$ represents a hydrogen atom);

[Formula 56]

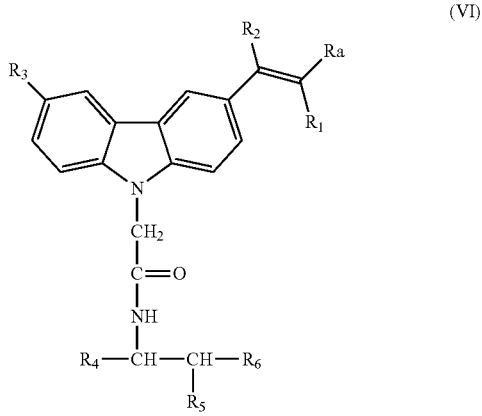

(VI)

(wherein R4, R5, R6 in formula VI represent the groups as described for the above formula V).

In the above synthetic pathway, the backbone structure of a moiety corresponding to a sugar structure in the resulting photoresponsive artificial nucleoside analogue molecule (VI) will be a structure which directly reflects the structure of an amine (V) used.

Accordingly, for example, D-threoninol may be used as the amine (V) in a case where a D-threoninol structure is desired as the backbone structure of the moiety corresponding to a sugar structure in the photoresponsive artificial nucleoside analogue molecule (VI). For example, L-threoninol may be used as the amine (V) in a case where an L-threoninol structure is desired. For example, serinol may be used as the amine (V) in a case where a serinol structure is desired. For example, (R)-3-amino-1,2-propanediol may be used as the amine (V) in a case where a (R)-3-amino-1,2-propanediol structure is desired. For example, (S)-3-amino-1,2-propanediol may be used as the amine (V) in a case where an (S)-3-amino-1,2-propanediol structure is desired.

The synthetic pathway described above is superior in that it has fewer steps to obtain the photoresponsive artificial nucleoside analog molecule (VI) from the modified vinylcarbazole molecule (VIII), it is simpler, and it can maintain a very high overall yield. Further, advantageously, a step requiring cautions and skills for operation such as an activation step with hydrogen chloride is not included in the synthetic pathway. In contrast, as a consequence of the presence of deoxyribose or ribose in the structure thereof, the synthetic pathway of a conventional photoreactive modified nucleoside molecule involves more steps and is more complicated as compared with the above synthetic pathway according to the present invention, and has an overall yield as low as a fraction of that of the above synthetic pathway according to the present invention. Further, as a consequence of the presence of deoxyribose or ribose in the structure thereof, the synthesis of a conventional photoreactive modified nucleoside molecule involves a step requiring cautions and skills for operation such as an activation step with hydrogen chloride for protecting and activating sugar hydroxy groups. Therefore, the compound according to the present invention is also superior in terms of easier synthesis and a higher overall yield as described above. Moreover, the present invention also relates to the above superior synthesis method (manufacturing method).

[Synthesis of a Monomer for Synthesizing a Modified Nucleic Acid and Synthesis of a Modified Nucleic Acid and the Like]

The monomer for synthesizing a modified nucleic acid according to the present invention can be obtained by the approach described in Scheme 1 shown below or an approach known to a person skilled in the art using the photoresponsive artificial nucleoside analog molecule (VI) which can be obtained from the above synthetic pathway. When the monomer for synthesizing a modified nucleic acid according to the present invention, which has a structure as described above, is used as a reagent for synthesizing nucleic acid by a known method such as the phosphoroamidite method and the H-phosphonate method, a nucleic acid or oligonucleotide in which the photoresponsive artificial nucleoside analog molecule (VI) is incorporated in a sequence (the modified nucleic acid and the like according to the present invention) can be obtained. As described above, the monomer for synthesizing a modified nucleic acid according to the present invention is superior in that it can be used as a reagent for synthesizing nucleic acid by a known method such as the phosphoroamidite method and the H-phosphonate method.

EXAMPLES

Below, the present invention will be described in detail with reference to Examples. The present invention shall not be limited to the Examples illustrated below.

Manufacturing Example 1

Synthesis of Nucleoside Analog (Photoreactive Element)

A photoresponsive artificial nucleoside analog molecule (which may be referred to as a nucleoside analog or a photoreactive element) as well as a monomer for synthesizing a modified nucleic acid were synthesized in accordance with the synthetic pathway shown in the following Scheme 1.

(Scheme 1)

[Formula 57]

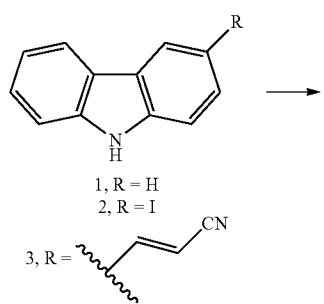

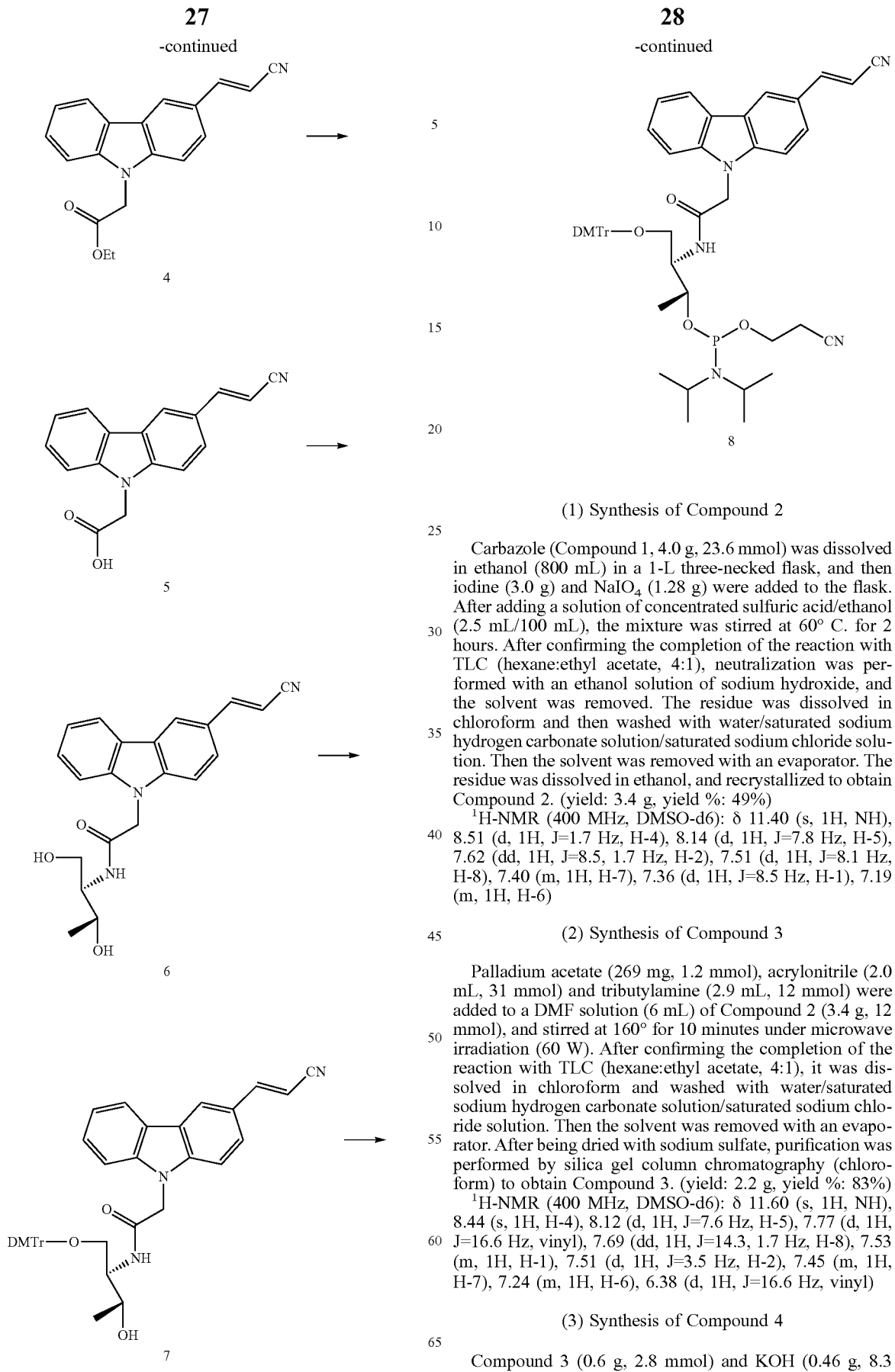

(1) Synthesis of Compound 2

Carbazole (Compound 1, 4.0 g, 23.6 mmol) was dissolved in ethanol (800 mL) in a 1-L three-necked flask, and then iodine (3.0 g) and NaIO$_4$ (1.28 g) were added to the flask. After adding a solution of concentrated sulfuric acid/ethanol (2.5 mL/100 mL), the mixture was stirred at 60° C. for 2 hours. After confirming the completion of the reaction with TLC (hexane:ethyl acetate, 4:1), neutralization was performed with an ethanol solution of sodium hydroxide, and the solvent was removed. The residue was dissolved in chloroform and then washed with water/saturated sodium hydrogen carbonate solution/saturated sodium chloride solution. Then the solvent was removed with an evaporator. The residue was dissolved in ethanol, and recrystallized to obtain Compound 2. (yield: 3.4 g, yield %: 49%)

$^1$H-NMR (400 MHz, DMSO-d6): δ 11.40 (s, 1H, NH), 8.51 (d, 1H, J=1.7 Hz, H-4), 8.14 (d, 1H, J=7.8 Hz, H-5), 7.62 (dd, 1H, J=8.5, 1.7 Hz, H-2), 7.51 (d, 1H, J=8.1 Hz, H-8), 7.40 (m, 1H, H-7), 7.36 (d, 1H, J=8.5 Hz, H-1), 7.19 (m, 1H, H-6)

(2) Synthesis of Compound 3

Palladium acetate (269 mg, 1.2 mmol), acrylonitrile (2.0 mL, 31 mmol) and tributylamine (2.9 mL, 12 mmol) were added to a DMF solution (6 mL) of Compound 2 (3.4 g, 12 mmol), and stirred at 160° for 10 minutes under microwave irradiation (60 W). After confirming the completion of the reaction with TLC (hexane:ethyl acetate, 4:1), it was dissolved in chloroform and washed with water/saturated sodium hydrogen carbonate solution/saturated sodium chloride solution. Then the solvent was removed with an evaporator. After being dried with sodium sulfate, purification was performed by silica gel column chromatography (chloroform) to obtain Compound 3. (yield: 2.2 g, yield %: 83%)

$^1$H-NMR (400 MHz, DMSO-d6): δ 11.60 (s, 1H, NH), 8.44 (s, 1H, H-4), 8.12 (d, 1H, J=7.6 Hz, H-5), 7.77 (d, 1H, J=16.6 Hz, vinyl), 7.69 (dd, 1H, J=14.3, 1.7 Hz, H-8), 7.53 (m, 1H, H-1), 7.51 (d, 1H, J=3.5 Hz, H-2), 7.45 (m, 1H, H-7), 7.24 (m, 1H, H-6), 6.38 (d, 1H, J=16.6 Hz, vinyl)

(3) Synthesis of Compound 4

Compound 3 (0.6 g, 2.8 mmol) and KOH (0.46 g, 8.3 mmol), tetrabutylammonium bromide (28 mg, 0.09 mmol)

were dissolved in acetone (15 mL), and stirred at 85° C. for 30 minutes. Ethyl bromoacetate (0.8 mL, 3.3 mmol) was added dropwise to the reaction solution, and then refluxed for 12 hours. After confirming the disappearance of the raw materials with TLC (chloroform:methanol, 9:1), the solvent was removed. The residue was then re-dissolved in chloroform and washed with water. The organic layer was concentrated with an evaporator, and purification was performed by silica gel column chromatography (chloroform). (yield: 0.72 g, 2.4 mmol, yield %: 85%)

1H-NMR (400 MHz, CDCl$_3$): δ 8.03-7.03 (m, 8H, ArH, ArCH), 5.87 (d, 0.85H, trans-CNCH), 5.35 (d, 1H, 0.15H, cis-CNCH), 5.00 (s, 2H, CH$_2$CO), 4.22 (q, 2H, CH3CH$_2$), 1.24 (t, 3H, CH$_3$). MALDI-TOF-MS: calcd.; 305.12 ([(M+H)$^+$]). found; 304.68.

(4) Synthesis of Compound 5

Compound 4 (0.12 g, 0.41 mmol) was dissolved in chloroform (6 mL), and methanol (7 mL) and water (3 mL) were added and stirred. Sodium hydroxide (0.39 g, 1 mmol) was further added, and stirred at room temperature for 4 hours. After confirming the disappearance of the raw materials with TLC, a methanol solution of hydrochloric acid was added to the reaction mixture to adjust a value of pH to 2. After being concentrated, it was dissolved in ethyl acetate, washed with water, then dried with magnesium sulfate. Then, purification was performed by silica gel column chromatography (chloroform:methanol, 7:3). (yield: 0.1 g, 0.34 mmol, yield %: 92%)

$^1$H-NMR (400 MHz, DMSO-d6): δ 8.4 (s, 1H, OH), 8.08-7.26 (m, 8H, Ar—H, ArCH), 6.4 (d, 0.92H, trans-CNCH), 5.7 (d, 0.08H, cis-CNCH), 4.8 (s, 2H, CH$_2$CO).

(5) Synthesis of Compound 6

D-threoninol (0.27 g, 2.7 mmol) was added to a DMF solution (20 mL) of Compound 5 (0.75 g, 2.7 mmol), WSC (0.5 g, 2.7 mmol), HOBt (0.35 g, 2.7 mmol), and stirred at room temperature for 24 hours. After confirming the disappearance of the raw materials with TLC (chloroform:methanol, 9:1), the reaction mixture solution was diluted with chloroform. This solution was washed with water and a saturated aqueous solution of sodium hydrogen carbonate, and then purification was performed by silica gel column chromatography (chloroform:methanol, 9:1). (yield: 0.92 g, 2.6 mmol, yield %: 94%)

$^1$H-NMR (400 MHz, DMSO-d6): δ 8.5 (s, 1H, NHCO), 8.0-7.2 (in, 8H, Ar—H, ArCH), 6.4 (d, 0.78H, trans-CNCH), 5.7 (d, 0.21H, cis-CNCH), 5.1 (t, 2H, CH$_2$CO), 4.7 (m, 2H, CH$_2$OH), 3.9 (m, 1H, NCH), 3.6 (q, 1H, CH$_2$OH), 3.5 (m, 1H, CHOH), 3.4 (m, 1H, CHOH), 1.0 (d, 3H, CH$_3$). MALDI-TOF-MS: calcd.; 363.15 [(M+H)$^+$]. found; 364.71.

(6) Synthesis of Compound 7

Compound 6 (0.95 g, 2.4 mmol) was added to a 100-mL two-necked eggplant-shaped flask, which was then purged with nitrogen. Then a pyridine solution (20 mL) of DMTrCl (0.90 g, 2.7 mmol), DMAP (60 mg, 0.49 mmol) was added dropwise, and stirred overnight at room temperature. After adding methanol to the reaction solution, an aqueous solution of sodium hydrogen carbonate was added, and extraction was performed with chloroform. The organic layer was then evaporated for concentration. The target substance was purified by silica gel column chromatography (0.2% trietylamine, 1% MeOH in CHCl$_3$). (yield: 0.86 g, 1.3 mmol, yield %: 54%)

$^1$H-NMR (400 MHz, CDCl$_3$): δ 8.1 (s, 1H, NHCO), 7.5-6.3 (m, 21H, Ar—H, ArCH), 5.8 (d, 0.9H, trans-CNCH), 5.3 (d, 0.1H, cis-CNCH), 4.9 (t, 2H, CH$_2$CO), 3.9 (m, 1H, CHOH), 3.8 (m, 1H, NCH), 3.74 (s, 6H, OCH$_3$), 3.1-3.2 (m, 2H, CH$_2$O), 2.7 (m, 1H, CHOH), 0.9 (d, 3H, CH$_3$).

(7) Synthesis of Compound 8

An anhydrous acetonitrile solution of Compound 7 (0.37 g, 0.55 mmol) was added to a rubber-sealed bottle (25 mL). After sealed, azeotropy was performed twice. Then the vessel was purged with nitrogen, and anhydrous acetonitrile (5.0 mL), 2-cyanoethyl-N,N,N',N'-tetraisopropylphosphor-diamidite (0.17 g, 0.55 mmol), 0.25 M BTT in MeCN (2.2 mL, 0.55 mmol) were added, and stirred at room temperature for 1 hour. After confirming the disappearance of the raw materials with TLC, the reaction mixture was diluted with de-acetec-acid-treated ethyl acetate, and washed with an aqueous solution of sodium hydrogen carbonate and an aqueous solution of sodium chloride. The organic layer was dried with anhydrous magnesium sulfate, and then filtration and solvent removal were performed to obtain Compound 8. (yield: 0.48 g, 0.52 mmol, yield %: 94%)

Manufacturing Example 2

Synthesis of Oligo DNA Comprising a Photoreactive Element

In accordance with the common cyanoethyl phosphoroamidite method, oligo DNA comprising a photoreactive element (which may be referred to as a nucleic acid photoreactive element/unit) was synthesized with an automated DNA synthesizer. The reaction time for a solid phase condensation reaction of Compound 8 only was set to 999 seconds. The coupling yield of Compound 8 was 97% or more as determined by tritylyl monitoring. Release from the solid phase and deprotection were performed with 28% aqueous ammonia, and then purification was performed by reversed-phase HPLC to obtain the target oligo DNA (5'-TGCAXCCGT-3', wherein X represents a nucleic acid photoreactive element). MALDI-TOF-MS analysis was performed for identification of the oligo DNA. ([(M+H)+]; Calcd. 2809.55. Found 2809.35).

Manufacturing Example 3

Synthesis of Oligo DNA Comprising a Conventional Photoreactive Modified Nucleoside For a control experiment, a compound represented by the following formula, 3-cyanovinylcarbazole-1'-β-deoxyriboside ($^{CNV}$K), was synthesized as a conventional photoreactive modified nucleoside comprising a vinylcarbazole backbone structure in place of the base moiety of a nucleobase and comprising deoxyribose at the deoxyribose moiety:

[Formula 58]

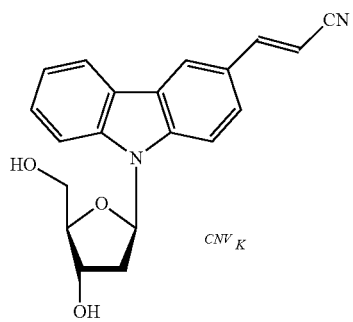

From this compound, a reagent for synthesizing nucleic acid represented by the following formula was synthesized:

[Formula 59]

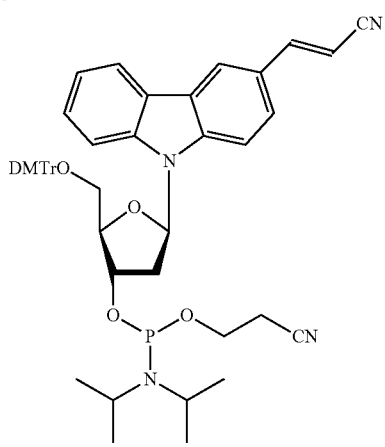

These syntheses were performed in accordance with the procedures in Scheme 1 from Example in Patent Literature 4 (Japanese Patent No. 4940311). Then, in accordance with the common cyanoethyl phosphoroamidite method, the oligo DNA (5'-TGCAXCCGT-3', wherein X is $^{CNV}$K) comprising a conventional photoreactive modified nucleoside was synthesized with an automated DNA synthesizer as described above.

[Evaluation of Photoreactivity]

Deoxyuridine (25 μM) was added as an internal standard to a mixture containing the oligo DNA comprising a photoreactive element obtained from Manufacturing Example 2 and a complementary oligo DNA (5'-ACGGGTGCA-3') in equal amount (5 μM in 50 mM Na-Cacodylate buffer (pH 7.4), 100 mM NaCl), and photoirradiation (366 nm, 1,600 mW/cm$^2$) was performed at 0° C. This solution was analyzed by UPLC (eluent: acetonitrile/50 mM ammonium formate, acetonitrile from 1 to 20% in 10 min, flow rate: 0.2 mL/min) to evaluate photoreactivity.

FIG. 1(a) is a diagram illustrating the above operation. In the modified ODN shown in the figure, the nucleoside analog (photoreactive element) according to the present invention is introduced as an improved photoreactive element at the position X in the sequence (Manufacturing Example 2). Further, the oligo DNA comprising a conventional photoreactive modified nucleoside obtained from Manufacturing Example 3 was used in a control experiment for comparison. In this case, $^{CNV}$K is introduced at the position X in the sequence.

FIG. 1(b) shows results from the UPLC analysis of the oligo DNA from Manufacturing Example 2 and the complementary oligo DNA after photoirradiation. Chromatograms piled in the direction of the vertical axis correspond to the durations of photoirradiation (0.0 second, 0.2 second, 0.5 second, 1.0 second, 3.0 seconds, 5.0 seconds, respectively), and the horizontal axis shows retention time (minutes). Two single-stranded ODNs (monomers) presented at the time before photoirradiation (0.0 second) was decreased due to photoirradiation, and at the same time, a photo dimer of the single-stranded ODNs was formed, and increased due to photoirradiation. FIG. 1(c) shows a graph illustrating these changes. The horizontal axis in FIG. 1(c) represents the duration of photoirradiation (seconds), and the vertical axis represents a conversion ratio (%). Open circles (○) represent the conventional type and closed squares (■) represents the improved type. With regard to the conversion rate, i.e., a rate of conversion of a monomer into a dimer, a conversion rate of 100% was assigned in the case of the complete conversion into a dimer. The nucleoside analog according to the present invention, i.e., an improved photoreactive element showed a conversion rate of as high as about 57% after 0.2 seconds, about 83% after 0.5 seconds and 96% after 1.0 second. In contrast, the conventional photoreactive modified nucleoside as a comparative example showed a conversion rate of about 35% after 0.2 seconds, about 71% after 0.5 seconds and 90% after 1.0 second. Even for the conversion rate of the conventional type, a sufficiently high conversion rate was achieved in a short time, as expected from a photochemical reaction. Nonetheless, the conversion rate of the improved type showed an about 1.6-times higher conversion rate at 0.2 seconds as compared with the conventional type.

[Comparison of Synthesis Yields]

Figure 2:
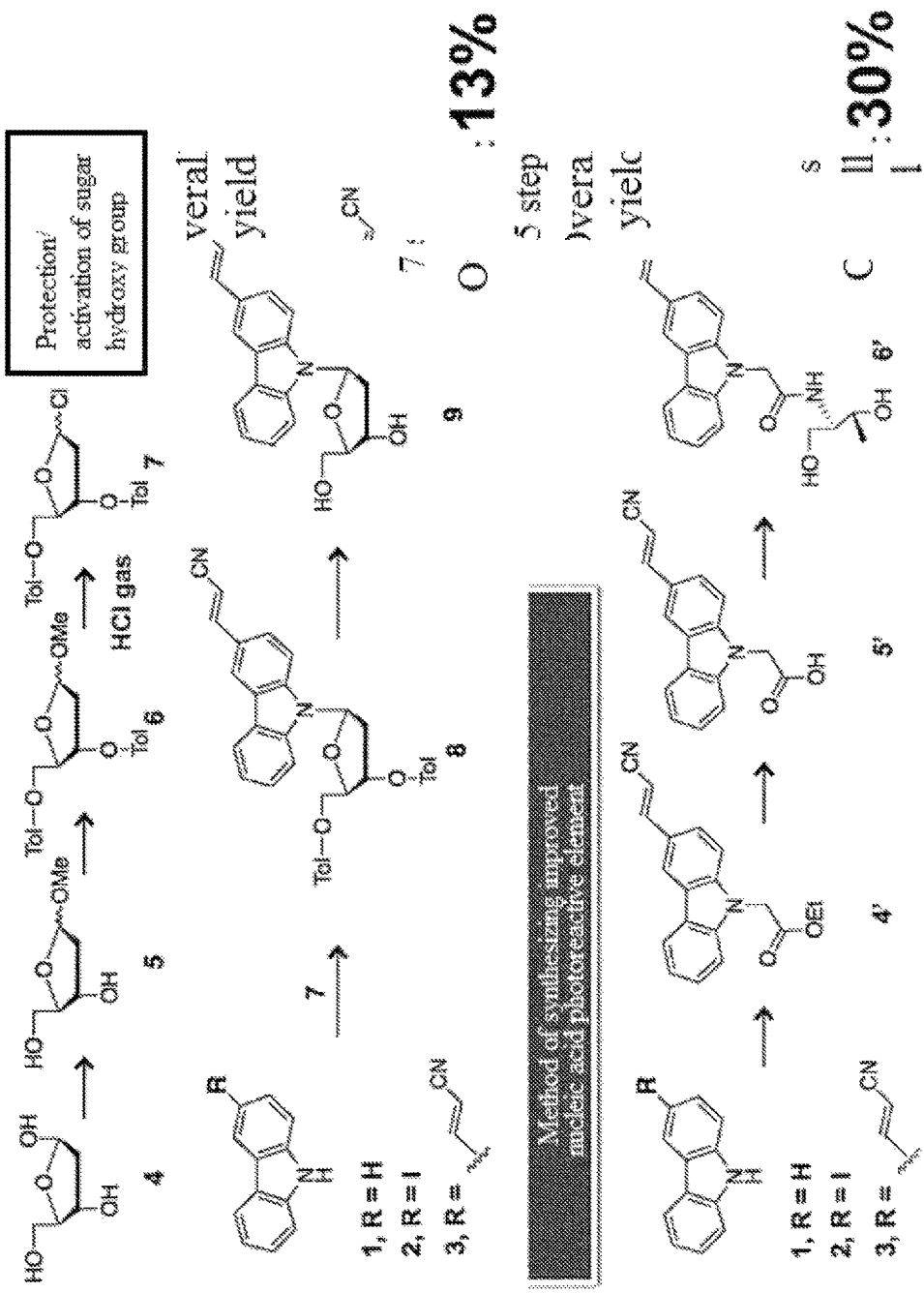
FIG. 2 shows the number of synthesis steps and overall yields.

The nucleoside analog (improved type) according to the present invention was able to be synthesized in accordance with the route/pathway shown in Scheme 1 described above. The synthesis involved 5 steps from an easily available start material, and the overall yield was 30%. In contrast, the conventional photoreactive modified nucleoside was able to be synthesized in accordance with the route described above. The synthesis involved 7 steps from an easily available start material, and the overall yield was 17%. FIG. 2 shows a diagram in which the steps and the overall yields of these syntheses were compared. As described above, the synthesis of the nucleoside analog according to the present invention involves fewer steps, and a higher overall yield of about 2.3-times can be achieved as compared with the synthesis of the conventional photoreactive modified nucleoside retaining a sugar structure. Further, advantageously, the synthesis of the nucleoside analog according to the present invention does not include a step requiring cautions and skills for operation in the synthetic pathway thereof, such as an activation step with hydrogen chloride which is required for the synthesis of a conventional photoreactive modified nucleoside retaining a sugar structure.

INDUSTRIAL APPLICABILITY

The present invention provides a novel photoreactive crosslinking agent which can be used in technologies for photoreactions of nucleic acid. The present invention is industrially useful.

The invention claimed is:
1. A photoreactive compound represented by the following formula I:

[Formula 1]

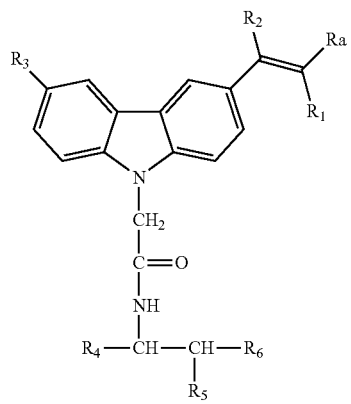

(wherein in the formula I,
Ra represents a cyano group, an amide group, a carboxyl group, a C2 to C7 alkoxycarbonyl group, a phosphono group, a sulfo group or a hydrogen atom,
R1 and R2 each independently represent a cyano group, an amide group, a carboxyl group, a C2 to C7 alkoxycarbonyl group or a hydrogen atom,
R3 is a hydrogen atom, a hydroxy group, a C1 to C3 alkoxy group, a C1 to C3 alkylsulfanyl group, a nitro group, a fluorine atom, a methyl fluoride group, a monovalent group of a C6 to C12 monocyclic or bicyclic aromatic compound, a monovalent group of a C6 to C12 monocyclic or bicyclic heterocyclic aromatic compound or a monovalent group represented by the following formula:

[Formula 2]

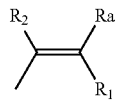

(wherein in the above formula, Ra, R1 and R2 represent groups selected from the groups listed for Ra, R1 and R2 described above with regard to the formula I independent of Ra, R1 and R2 described above with regard to the formula I),
R4 represents a hydrogen atom or a $Q_1$-O—$CH_2$-group,
R5 represents an —O-$Q_1$ group, a hydrogen atom, a methyl group or an ethyl group (provided that R5 represents an —O-$Q_1$ group when R4 is a hydrogen atom, and
R5 represents a hydrogen atom, a methyl group or an ethyl group when R4 is a $Q_1$-O—$CH_2$-group),
R6 represents an —O-$Q_2$ group, a —$CH_2$—O-$Q_2$ group or a —$CH(CH_3)$—O-$Q_2$ group,
$Q_1$ represents a hydrogen atom, a phosphate group formed together with O attached to $Q_1$, a nucleotide or nucleic acid linked through a phosphodiester bond formed with a phosphate group formed together with O attached to $Q_1$ or a DMTr group,
$Q_2$ represents a hydrogen atom, a phosphate group formed together with O attached to $Q_2$, a nucleotide or nucleic acid linked through a phosphodiester bond formed with a phosphate group formed together with O attached to $Q_2$, a group represented by the following formula:

[Formula 3]

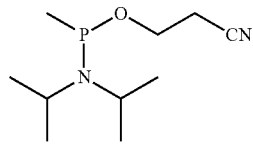

(wherein the above formula represents a monovalent group having a free valency at P), or a group represented by the following formula:

[Formula 4]

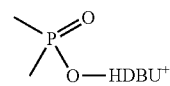

(wherein the above formula represents a monovalent group having a free valency at P), and
wherein at least one of $Q_1$ and $Q_2$ is the nucleotide or nucleic acid linked through the phosphodiester bond formed with the phosphate group together with O).

2. The compound according to claim 1, represented by the following formula II:

[Formula 5]

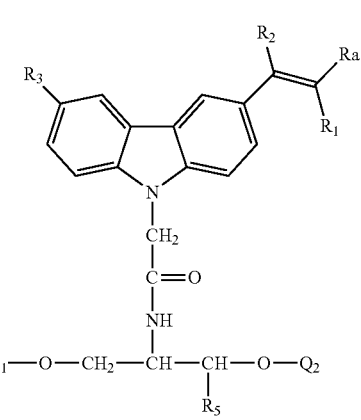

(wherein in the formula II,
Ra represents a cyano group, an amide group, a carboxyl group, a C2 to C7 alkoxycarbonyl group, a phosphono group, a sulfo group or a hydrogen atom,
R1 and R2 each independently represent a cyano group, an amide group, a carboxyl group, a C2 to C7 alkoxycarbonyl group or a hydrogen atom,
R3 is a hydrogen atom, a hydroxy group, a C1 to C3 alkoxy group, a C1 to C3 alkylsulfanyl group, a nitro group, a fluorine atom, a methyl fluoride group, a monovalent group of a C6 to C12 monocyclic or bicyclic aromatic compound, a monovalent group of a C6 to C12 monocyclic or bicyclic heterocyclic aromatic compound or a monovalent group represented by the following formula:

[Formula 6]

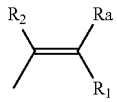

(wherein in the above formula, Ra, R1 and R2 represent groups selected from the groups listed for Ra, R1 and R2 described above with regard to the formula I independent of Ra, R1 and R2 described above with regard to the formula I), R5 represents a hydrogen atom, a methyl group or an ethyl group, $Q_1$ represents a hydrogen atom, a phosphate group formed together with O attached to $Q_1$, a nucleotide or nucleic acid linked through a phosphodiester bond formed with a phosphate group formed together with O attached to $Q_1$ or a DMTr group, $Q_2$ represents a hydrogen atom, a phosphate group formed together with O attached to $Q_2$, a nucleotide or nucleic acid linked through a phosphodiester bond formed with a phosphate group formed together with O attached to $Q_2$, a group represented by the following formula:

[Formula 7]

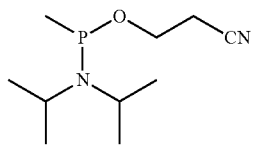

(wherein the above formula represents a monovalent group having a free valency at P), or a group represented by the following formula:

[Formula 8]

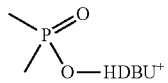

(wherein the above formula represents a monovalent group having a free valency at P)).

3. The compound according to claim 1, wherein R3 is a hydrogen atom, a hydroxy group, a C1 to C3 alkoxy group, a C1 to C3 alkylsulfanyl group, a nitro group, a fluorine atom, a trifluoromethyl group, a phenyl group, a 2-naphthyl group, a 2-indolyl group, a benzimidazole-2-yl group or a benzothiophene-2-yl group.

4. A photoreactive crosslinking agent comprising the compound according to claim 1.

5. A method of forming photo crosslinking, comprising: crosslinking a nucleobase having a pyrimidine ring to the compound according to claim 1.

6. The compound according to claim 2, wherein R3 is a hydrogen atom, a hydroxy group, a C1 to C3 alkoxy group, a C1 to C3 alkylsulfanyl group, a nitro group, a fluorine atom, a trifluoromethyl group, a phenyl group, a 2-naphthyl group, a 2-indolyl group, a benzimidazole-2-yl group or a benzothiophene-2-yl group.

7. A photoreactive crosslinking agent comprising the compound according to claim 2.

8. A photoreactive crosslinking agent comprising the compound according to claim 3.

9. A method of forming photo crosslinking, comprising: crosslinking a nucleobase having a pyrimidine ring to the compound according to claim 2.

10. A method of forming photo crosslinking, comprising: crosslinking a nucleobase having a pyrimidine ring to the compound according to claim 3.

11. A method of producing the photoreactive compound of claim 1, comprising a step of:
incorporating a photoreactive compound into a DNA, the photoreactive compound being represented by the following formula I:

[Formula 1]

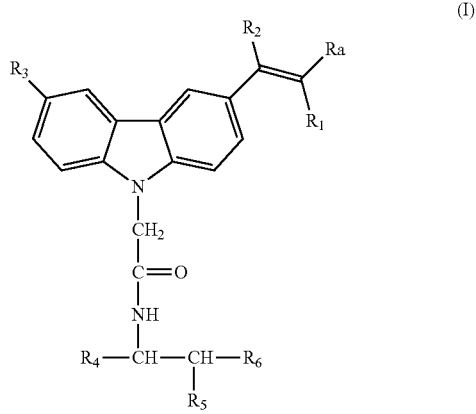

(I)

(wherein in the formula I,
Ra represents a cyano group, an amide group, a carboxyl group, a C2 to C7 alkoxycarbonyl group, a phosphono group, a sulfo group or a hydrogen atom,
R1 and R2 each independently represent a cyano group, an amide group, a carboxyl group, a C2 to C7 alkoxycarbonyl group or a hydrogen atom,
R3 is a hydrogen atom, a hydroxy group, a C1 to C3 alkoxy group, a C1 to C3 alkylsulfanyl group, a nitro group, a fluorine atom, a methyl fluoride group, a monovalent group of a C6 to C12 monocyclic or bicyclic aromatic compound, a monovalent group of a C6 to C12 monocyclic or bicyclic heterocyclic aromatic compound or a monovalent group represented by the following formula:

[Formula 2]

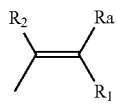

(wherein in the above formula, Ra, R1 and R2 represent groups selected from the groups listed for Ra, R1 and R2 described above with regard to the formula I independent of Ra, R1 and R2 described above with regard to the formula I), R4 represents a hydrogen atom or a $Q_1$-O—$CH_2$-group, R5 represents an —O-$Q_1$ group, a hydrogen atom, a methyl group or an ethyl group (provided that R5 represents an —O-$Q_1$ group when R4 is a hydrogen atom, and R5 represents a hydrogen atom, a methyl group or an ethyl group when R4 is a $Q_1$-O—$CH_2$-group), R6 represents an —O-$Q_2$ group, a —$CH_2$—O—$O_2$ group or a —$CH(CH_3)$—O—$O_2$ group, $Q_1$ represents a hydrogen atom, a phosphate group formed together with O attached to a nucleotide or nucleic acid linked through a phosphodiester bond formed with a phosphate group formed together with O attached to $Q_1$ or a DMTr group, $Q_2$ represents a hydrogen atom, a phosphate group formed together with O attached to $Q_2$, a nucleotide or nucleic acid linked through a phosphodiester bond formed with a phosphate group formed together with 0 attached to $Q_2$, a group represented by the following formula:

[Formula 3]

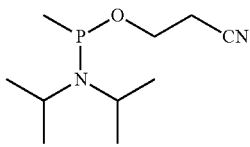

(wherein the above formula represents a monovalent group having a free valency at P), or a group represented by the following formula:

[Formula 4]

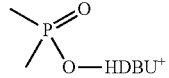

(wherein the above formula represents a monovalent group having a free valency at P), and wherein $Q_1$ is a DMTr group and $Q_2$ is a group represented by the following formula:

[Formula 3]

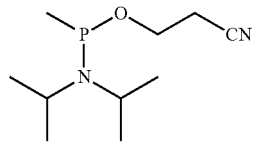

(wherein the above formula represents a monovalent group having a free valency at P).

12. The method of claim 11, wherein the step of incorporating the photoreactive compound into the DNA is performed by a phosphoroamidite method and/or a H-phosphonate method.

* * * * *

UNITED STATES PATENT AND TRADEMARK OFFICE
CERTIFICATE OF CORRECTION

PATENT NO. : 10,450,334 B2
APPLICATION NO. : 14/780187
DATED : October 22, 2019
INVENTOR(S) : Kenzo Fujimoto et al.

Page 1 of 1

It is certified that error appears in the above-identified patent and that said Letters Patent is hereby corrected as shown below:

In the Claims

Column 37 Line 11 & 12:
Change:
$Q_1$ represents a hydrogen atom, a phosphate group formed together with O attached to a nucleotide or nucleic acid To Be:
$Q_1$ represents a hydrogen atom, a phosphate group formed together with O attached to $Q_1$, a nucleotide or nucleic acid Column 37 Line 19 & 20:
Change:
a phosphate group formed together with 0 attached to Qz, a group represented by the following formula:

To Be:
a phosphate group formed together with O attached to $Q_2$, a group represented by the following formula:

Signed and Sealed this
Thirty-first Day of December, 2019

Andrei Iancu
*Director of the United States Patent and Trademark Office*